(12) United States Patent
Shelton, IV et al.

(10) Patent No.: US 10,905,421 B2
(45) Date of Patent: Feb. 2, 2021

(54) ELECTRICALLY-POWERED SURGICAL BOX STAPLERS

(71) Applicant: Ethicon LLC, Guaynabo, PR (US)

(72) Inventors: Frederick E. Shelton, IV, Hillsboro, OH (US); Michael J. Vendely, Lebanon, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 444 days.

(21) Appl. No.: 15/689,104

(22) Filed: Aug. 29, 2017

(65) Prior Publication Data

US 2019/0059888 A1 Feb. 28, 2019

(51) Int. Cl.
*A61B 17/072* (2006.01)
*A61B 17/068* (2006.01)
(Continued)

(52) U.S. Cl.
CPC .... *A61B 17/07207* (2013.01); *A61B 17/0684* (2013.01); *A61B 17/115* (2013.01);
(Continued)

(58) Field of Classification Search
CPC ............ A61B 17/07207; A61B 17/068; A61B 17/0684; A61B 17/072; A61B 17/115;
(Continued)

(56) References Cited

U.S. PATENT DOCUMENTS 5,322,055 A 6/1994 Davison et al.
5,558,671 A 9/1996 Yates
(Continued)

FOREIGN PATENT DOCUMENTS

WO 2014151621 A1 9/2014
WO 2014151952 A1 9/2014

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — Hemant Desai
*Assistant Examiner* — Jacob A Smith
(74) *Attorney, Agent, or Firm* — Mintz Levin Cohn Ferris Glovsky and Popeo P.C.

(57) ABSTRACT

Systems and methods for stapling tissue during surgery are provided. In one exemplary embodiment, a surgical stapling system is provided that includes a staple shaft assembly having a staple advancing and forming assembly and a shaft with a plurality of staples, a drive system operably coupled to the staple shaft assembly and operably coupled to at least one motor, and a control system. The drive system can have a plurality of stages of operation that drive the staple advancing and forming assembly to form a staple around tissue. The control system can be configured to actuate the at least one motor to drive the drive system and thereby control movement of the staple advancing and forming assembly and to modify a force applied to the drive system by the at least one motor during at least one stage of operation based on at least one predetermined threshold.

20 Claims, 7 Drawing Sheets

(51) Int. Cl.
*A61B 17/00* (2006.01)
*A61B 17/115* (2006.01)
*A61B 90/00* (2016.01)

(52) U.S. Cl.
CPC .............. *A61B 2017/00017* (2013.01); *A61B 2017/00398* (2013.01); *A61B 2090/064* (2016.02); *A61B 2090/066* (2016.02)

(58) Field of Classification Search
CPC ........ A61B 2090/064; A61B 2090/066; A61B 2017/00017; A61B 2017/00398; A61B 17/0682; A61B 17/0686
USPC ................................ 227/175.1, 175.3, 178.1
See application file for complete search history.

(56) References Cited

U.S. PATENT DOCUMENTS

| | | |
|---|---|---|
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,039,735 A | 3/2000 | Greep |
| 6,066,137 A | 5/2000 | Greep |
| 6,132,368 A * | 10/2000 | Cooper .................. A61B 46/13 600/102 |
| 6,168,605 B1 | 1/2001 | Measamer et al. |
| 6,231,565 B1 | 5/2001 | Tovey et al. |
| 6,325,811 B1 | 12/2001 | Messerly |
| 6,364,888 B1 | 4/2002 | Niemeyer et al. |
| 6,500,176 B1 | 12/2002 | Truckai et al. |
| 6,783,524 B2 * | 8/2004 | Anderson ............... A61B 34/70 606/28 |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckal et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,455,208 B2 | 11/2008 | Wales et al. |
| 7,506,790 B2 | 3/2009 | Shelton, IV |
| 7,524,320 B2 | 4/2009 | Tierney et al. |
| 7,549,564 B2 | 6/2009 | Boudreaux |
| 7,559,450 B2 | 7/2009 | Wales et al. |
| 7,654,431 B2 | 2/2010 | Hueil et al. |
| 7,691,098 B2 | 4/2010 | Wallace et al. |
| 7,780,054 B2 | 8/2010 | Wales |
| 7,784,662 B2 | 8/2010 | Wales et al. |
| 7,798,386 B2 | 9/2010 | Schall et al. |
| 7,806,891 B2 | 10/2010 | Nowlin et al. |
| 7,824,401 B2 | 11/2010 | Manzo et al. |
| 8,439,910 B2 | 5/2013 | Greep et al. |
| 8,461,744 B2 | 6/2013 | Wiener et al. |
| 8,469,252 B2 * | 6/2013 | Holcomb ........... A61B 17/0684 227/175.1 |
| 8,602,286 B2 * | 12/2013 | Crainich ............ A61B 17/0682 227/175.1 |
| 8,684,253 B2 | 4/2014 | Giordano et al. |
| 8,771,270 B2 | 7/2014 | Burbank |
| 8,986,302 B2 | 3/2015 | Aldridge et al. |
| 9,023,071 B2 | 5/2015 | Miller et al. |
| 9,072,536 B2 * | 7/2015 | Shelton, IV ........... A61B 34/30 |
| 9,095,367 B2 | 8/2015 | Olson et al. |
| 9,119,657 B2 | 9/2015 | Shelton, IV et al. |
| 9,168,092 B2 | 10/2015 | Horner et al. |
| 9,393,037 B2 | 7/2016 | Olson et al. |
| 9,445,816 B2 | 9/2016 | Swayze et al. |
| 9,585,658 B2 | 3/2017 | Shelton, IV |
| 9,713,468 B2 | 7/2017 | Harris et al. |
| 9,713,471 B2 | 7/2017 | Holcomb et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2010/0191282 A1 * | 7/2010 | Harris ................ A61B 17/0644 606/219 |
| 2010/0198248 A1 | 8/2010 | Vakharia |
| 2011/0015631 A1 | 1/2011 | Wiener et al. |
| 2011/0087218 A1 | 4/2011 | Boudreaux et al. |
| 2011/0087256 A1 | 4/2011 | Wiener et al. |
| 2011/0290856 A1 * | 12/2011 | Shelton, IV ........... A61B 34/76 227/180.1 |
| 2012/0078139 A1 | 3/2012 | Aldridge et al. |
| 2012/0078243 A1 | 3/2012 | Worrell et al. |
| 2012/0078247 A1 | 3/2012 | Worrell et al. |
| 2012/0116379 A1 | 5/2012 | Yates et al. |
| 2012/0203168 A1 * | 8/2012 | Fujimoto ............. G09B 23/285 604/95.01 |
| 2012/0248167 A1 * | 10/2012 | Flanagan ............. A61B 17/068 227/2 |
| 2012/0292367 A1 | 11/2012 | Morgan et al. |
| 2013/0012957 A1 | 1/2013 | Shelton, IV et al. |
| 2013/0023868 A1 | 1/2013 | Worrell et al. |
| 2013/0030428 A1 | 1/2013 | Worrell et al. |
| 2013/0172901 A1 * | 7/2013 | Bozorg Grayeli ........ A61F 2/18 606/108 |
| 2013/0261648 A1 | 10/2013 | Laurent et al. |
| 2013/0325034 A1 | 12/2013 | Schena et al. |
| 2014/0005718 A1 * | 1/2014 | Shelton, IV ........... A61B 34/35 606/205 |
| 2014/0148819 A1 * | 5/2014 | Inoue ............... A61B 17/32002 606/130 |
| 2014/0151952 A1 | 6/2014 | Kozaki |
| 2014/0166728 A1 | 6/2014 | Swayze et al. |
| 2014/0171970 A1 | 6/2014 | Martin et al. |
| 2014/0246476 A1 * | 9/2014 | Hall ...................... A61B 90/90 227/175.1 |
| 2014/0263538 A1 * | 9/2014 | Leimbach .......... A61B 17/0686 227/175.1 |
| 2014/0263541 A1 | 9/2014 | Leimbach et al. |
| 2014/0276931 A1 | 9/2014 | Parihar et al. |
| 2015/0053744 A1 * | 2/2015 | Swayze ................... G06T 11/60 227/176.1 |
| 2015/0209059 A1 | 7/2015 | Trees et al. |
| 2015/0209573 A1 | 7/2015 | Hibner et al. |
| 2015/0272572 A1 * | 10/2015 | Overmyer ............. G16H 40/63 227/177.1 |
| 2015/0272575 A1 | 10/2015 | Leimbach et al. |
| 2015/0282825 A1 | 10/2015 | Trees et al. |
| 2015/0365296 A1 | 12/2015 | Bunte et al. |
| 2016/0019918 A1 | 1/2016 | Juman |
| 2016/0019919 A1 | 1/2016 | Gale et al. |
| 2016/0089533 A1 | 3/2016 | Turner et al. |
| 2016/0175060 A1 | 6/2016 | Park |
| 2016/0270780 A1 * | 9/2016 | Hall ...................... A61B 34/74 |
| 2016/0287252 A1 | 10/2016 | Parihar |
| 2016/0367243 A1 | 12/2016 | Martin et al. |
| 2017/0056038 A1 | 3/2017 | Hess et al. |
| 2017/0196637 A1 | 7/2017 | Shelton, IV et al. |
| 2017/0202609 A1 | 7/2017 | Shelton, IV et al. |
| 2017/0296183 A1 * | 10/2017 | Shelton, IV ..... A61B 17/07207 |

OTHER PUBLICATIONS

U.S. Appl. No. 15/237,653 entitled "Methods, Systems, and Devices for Controlling a Motor of a Robotic Surgical System" filed Aug. 16, 2016.

U.S. Appl. No. 15/422,767 entitled "Robotic Surgical System and Methods for Articulation Calibration" filed Feb. 2, 2017.

U.S. Appl. No. 15/634,620 entitled "Surgical Stapler with Independently Actuated Drivers to Provide Varying Staple Heights" filed Jun. 27, 2017.

U.S. Appl. No. 15/674,075 entitled "Clip Retention for Surgical Clip Applier" filed Aug. 10, 2017.

(56) References Cited

OTHER PUBLICATIONS

U.S. Appl. No. 15/674,086 entitled "Surgical Clip Applier Jaw Alignment" filed Aug. 10, 2017.
U.S. Appl. No. 15/674,096 entitled "Surgical Device with Overload Mechanism" filed Aug. 10, 2017.
U.S. Appl. No. 15/674,121 entitled "Jaw for Clip Applier" filed Aug. 10, 2017.
U.S. Appl. No. 15/674,125 entitled "Clip Appliers with Extended Jaw Tip" filed Aug. 10, 2017.
U.S. Appl. No. 15/674,166 entitled "Surgical Clip Applier" filed Aug. 10, 2017.
U.S. Appl. No. 15/689,072 entitled "Methods, Systems, and Devices for Controlling Electrosurgical Tools" filed Aug. 29, 2017.
U.S. Appl. No. 29/613,511 entitled "Clip Applier Rotation Knob" filed Aug. 10, 2017.

* cited by examiner

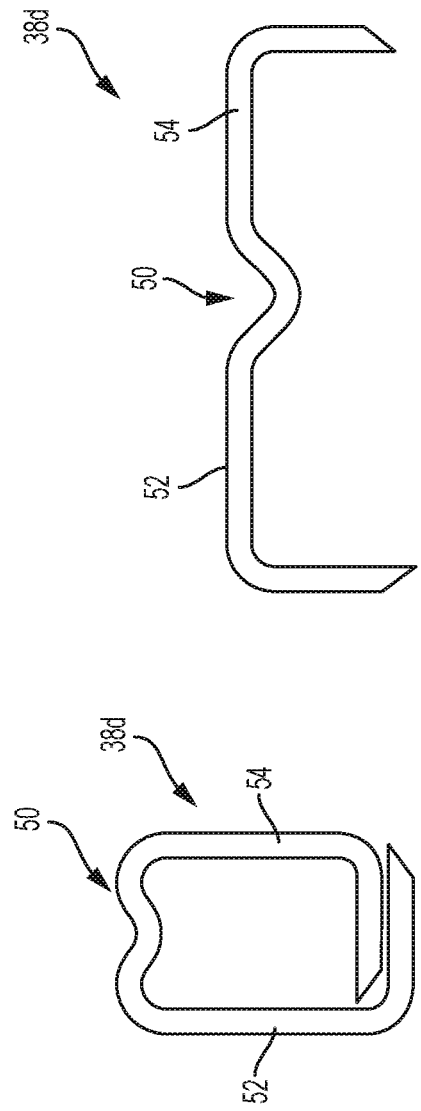
FIG. 3A
FIG. 3B
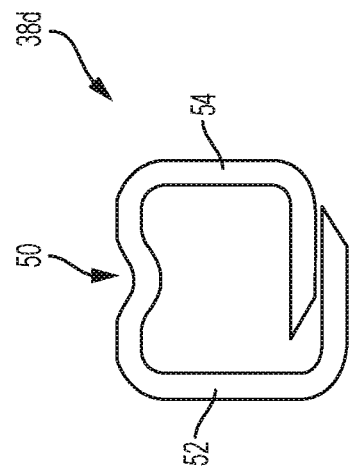
FIG. 3C

ELECTRICALLY-POWERED SURGICAL BOX STAPLERS

FIELD

Controls systems and methods for controlling electrically-powered surgical staplers are provided for binding or joining tissue to itself, another tissue, or a structure during a surgical procedure.

BACKGROUND

More and more surgical procedures are being performed using electrically-powered surgical devices that are either hand-held or that are coupled to a surgical robotic system. Such devices generally include one or more motors for driving various functions on the device, such as shaft rotation, articulation of an end effector, scissor or jaw opening and closing, firing or clips, staples, cutting elements, and/or energy, etc.

A common concern with electrically-powered surgical devices is the lack of control and tactile feedback that is inherent to a manually-operated device. Surgeons and other users accustomed to manually-operated devices often find that electrically-powered devices reduce their situational awareness because of the lack of feedback from the device. For example, electrically-powered devices do not provide users with any feedback regarding the progress of a cutting and/or sealing operation (e.g., an actuation button or switch is typically binary and provides no feedback on how much tissue has been cut, etc.) or the forces being encountered (e.g., toughness of the tissue). This lack of feedback can produce undesirable conditions. For example, if a motor's power is not adequate to perform the function being actuated, the motor can stall out. Without any feedback to a user, the user may maintain power during a stall, potentially resulting in damage to the device and/or the patient. Furthermore, even if the stall is discovered, users often cannot correct the stall by reversing the motor because a greater amount of force is available to actuate than may be available to reverse it (e.g., due to inertia when advancing). As a result, time-intensive extra operations can be required to disengage the device from the tissue.

In addition, electrically-powered devices can be less precise in operation than manually-operated devices. For example, users of manually-operated devices are able to instantly stop the progress of a mechanism by simply releasing the actuation mechanism. With an electrically-powered device, however, releasing an actuation button or switch may not result in instantaneous halting of a mechanism, as the electric motor may continue to drive the mechanism until the kinetic energy of its moving components is dissipated. As a result, a mechanism may continue to advance for some amount of time even after a user releases an actuation button.

Accordingly, there remains a need for improved devices and methods that address current issues with electrically-powered surgical devices.

SUMMARY

Surgical stapling systems and methods for using the same are provided herein.

In one exemplary embodiment, a surgical stapling system is provided and can include a staple shaft assembly having a shaft with a plurality of staples disposed therein in a closed configuration and staple advancing and forming assembly. A drive system can be operably coupled between at least one motor and the staple advancing and forming assembly, and a control system can be configured to actuate the at least one motor to drive the drive system and thereby control movement of the staple advancing and forming assembly.

The drive system can have multiple stages of operation. For example, the stages of operation can include a first stage of operation in which the drive system drives the staple advancing and forming assembly to advance a distal-most staple of the plurality of staples, a second stage of operation in which the drive system drives the staple advancing and forming assembly to move the distal-most staple from the closed configuration to an open configuration, and a third stage of operation in which the drive system drives the staple advancing and forming assembly to form the distal-most staple around tissue. In one embodiment, the drive system can also have a fourth stage of operation in which the drive system proximally retracts the staple advancing and forming assembly to release the distal-most staple.

The control system can have at least one predetermined motor force threshold for at least one stage of operation of the drive system. For example, when the drive system includes first, second, and third stages of operation, the control system can includes at least one predetermined motor force threshold for at least one of the first, second, and third stages of operation, and the control system can be configured to modify a force applied to the drive system by the at least one motor during the at least one stage of operation based on the at least one predetermined motor force threshold. In one embodiment, the at least one predetermined motor force threshold includes a maximum motor force threshold for each of the first, second, and third stages of operation. In such instances, the control system can be configured to stop movement of the drive system when the motor force exceeds the maximum motor force threshold during at least one of the first, second, and third stages.

The staple advancing and forming assembly can have a variety of configurations. In one embodiment, the staple advancing and forming assembly can include a staple advancing assembly having a pusher and an anvil. The stapling advancing assembly can be configured to distally advance the distal-most staple of the plurality of staples and configured to move the distal-most staple from the closed configuration to the open configuration. The staple advancing and forming assembly can also include a staple former. The staple former can be configured to form the distal-most staple around tissue. In one aspect, during the first stage of operation, the drive system can drive the pusher distally from a proximal position to an intermediate position and can drive the anvil from a proximal position to a distal-most position. In another aspect, during the second stage of operation, the drive system can drive the pusher distally from the intermediate position to a distal-most position such that the distal-most staple can be moved from the closed configuration to the open configuration. In yet another aspect, during the third stage of operation, the drive system can drive the staple former.

In one aspect, when the drive system includes the fourth stage of operation, the staple advancing and forming assembly can include a staple former that forms the distal-most staple around tissue, and, during the fourth stage of operation, the drive system can proximally retract the staple former to release the distal-most staple. In another aspect, the control system can have a predetermined minimum force threshold during the fourth stage of operation, and the control system can be configured to stop proximal retraction of the staple advancing and forming assembly when the motor force is less than the minimum motor force threshold.

In another exemplary embodiment, a surgical stapling system is provided and can include an electromechanical tool shaft assembly, a drive system that can be operably coupled to the electromechanical tool shaft assembly and to at least one motor, and a control system. The electromechanical tool shaft assembly can have an instrument shaft, a discharge channel at a distal end thereof, and a staple stack disposed within the instrument shaft and can include a plurality of staples in a folded delivery configuration. The electromechanical tool shaft assembly can also include a staple advancing assembly, which extends through the instrument shaft, and a staple forming assembly. The staple advancing assembly can be configured to feed a distal-most staple of the staple stack into the discharge channel and to move the distal-most staple from the folded delivery configuration into an open configuration. The staple forming assembly can be configured to move the distal-most staple from the open configuration to a tissue-engaging configuration. The at least one motor can be configured to drive the staple advancing assembly and the staple forming assembly.

The drive system can have multiple stages of operation. For example, the stages of operation can include a first stage of operation in which the drive system drives the staple advancing assembly to advance the distal-most staple of the plurality of staples, a second stage of operation in which the drive system drives the staple advancing assembly to move the distal-most staple from the closed configuration to an open configuration, and a third stage of operation in which the drive system drives the staple forming assembly to move the distal-most staple from the open configuration to a tissue-engaging configuration. In one embodiment, the drive system is disposed within a housing coupled to a proximal end of the instrument shaft. In another embodiment, the drive system includes a first housing on a robotic arm having the at least one motor disposed therein, and a second housing on a proximal end of the instrument shaft and having at least one connector for coupling to the at least one motor in the first housing.

The control system can be configured to actuate the drive system and thereby control movement of the staple advancing assembly and the staple forming assembly. In one aspect, control system can have at least one predetermined motor force threshold for at least one stage of operation of the drive system. For example, when the drive system includes first, second, and third stages of operation, the control system can include at least one predetermined motor force threshold for at least one of the first, second, and third stages of operation. The control system can be configured to modify a force applied to the drive system by the at least one motor during the at least one stage of operation based on the at least one predetermined motor force threshold. In one embodiment, the at least one predetermined motor force threshold includes a maximum motor force threshold for each of the first, second, and third stages of operation. In such instances, the control system can be configured to stop movement of the drive system when the motor force exceeds the maximum motor force threshold during at least one of the first, second, and third stages.

Methods for stapling tissue are also provided. In one embodiment, the method can include actuating a drive system having a control system operably coupled thereto, to thereby cause a staple advancing assembly to move a distal-most staple seated within a discharge channel on a distal end of a stapling device from a folded delivery configuration into an open configuration. The method can also include manipulating the stapling device to position tissue within the distal-most staple and actuating the drive system to cause a staple forming assembly to move the distal-most staple from the open configuration to a tissue-engaging configuration thereby engaging the tissue positioned therein. The control system can monitor a force on at least one motor, which is operable coupled to the drive system, during actuation of the drive system and the control system can modify the force applied to the drive system by the at least one motor during at least one stage of operation based on at least one predetermined motor force threshold.

In one embodiment, the at least one predetermined motor force threshold can include a maximum motor force for at least one stage of operation. In such instances, the method can also include ceasing movement of the drive system when the force applied to the drive system exceeds the maximum motor force during the at least one stage of operation. The step of ceasing movement of the drive system can include stopping distal movement of the staple advancing assembly or the staple forming assembly.

In another embodiment, the at least one predetermined motor threshold can include a minimum motor force for at least one stage of operation. In such instances, the method can also include ceasing movement of the drive system when the force applied to the drive system is less than the minimum motor threshold. The step of ceasing movement of the drive system can include stopping proximal retraction of the stable forming assembly.

BRIEF DESCRIPTION OF THE DRAWINGS

This invention will be more fully understood from the following detailed description taken in conjunction with the accompanying drawings, in which:

FIG. 3A is a top view of an exemplary staple in a closed configuration that can be disposed within the staple shaft assembly of the surgical stapler of FIG. 1;

FIG. 3B is a top view of the staple of FIG. 3A shown in an open configuration;

FIG. 3C is a top view of the staple of FIG. 3A shown in a tissue-engaging configuration;

DETAILED DESCRIPTION

Figure 1:
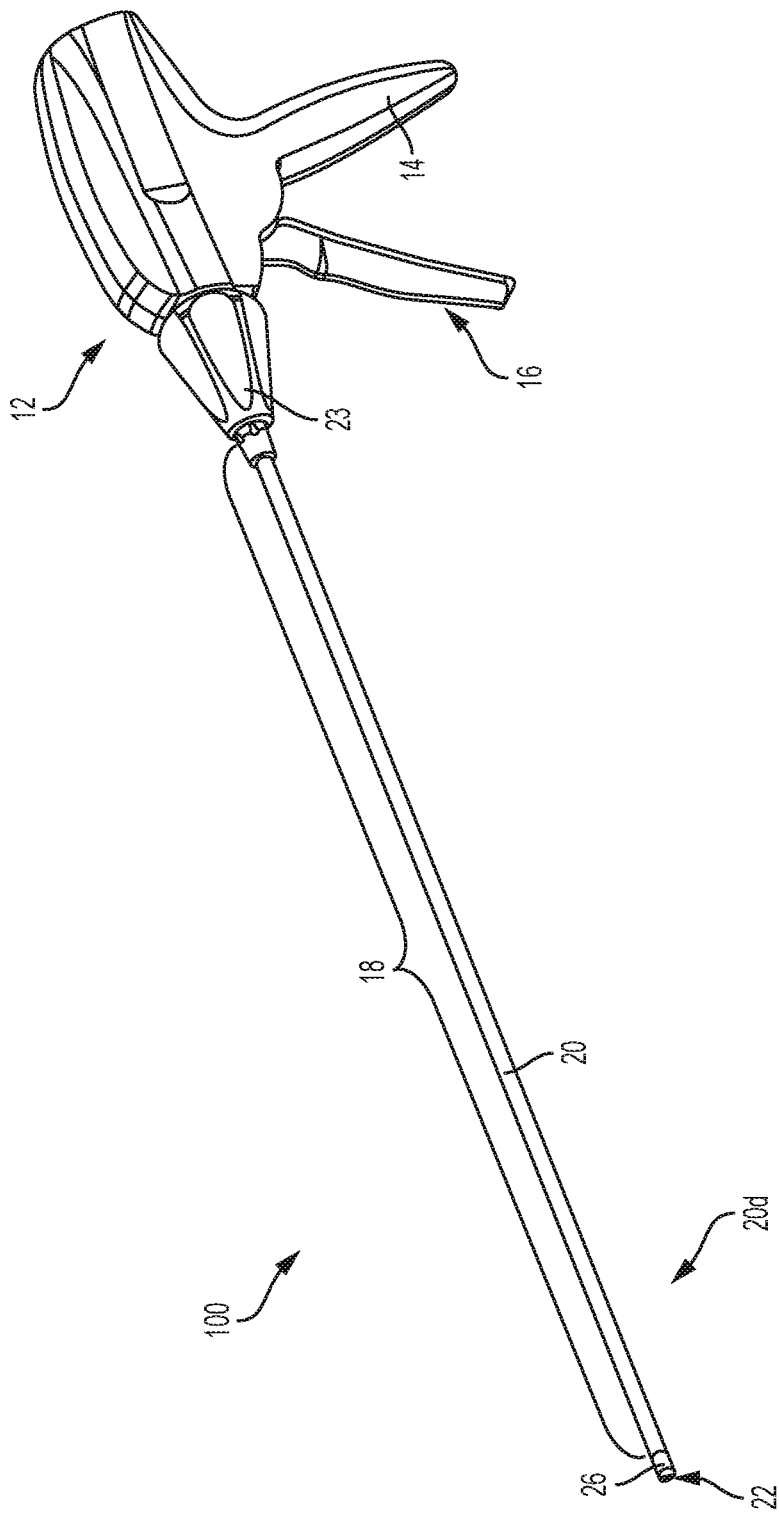
FIG. 1 is a side view of one exemplary embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Control systems and methods are provided for controlling electrically powered surgical devices that can bind or join tissue to itself, another tissue, or a structure during a surgical procedure. In an exemplary embodiment, a surgical stapling system generally includes a staple shaft assembly having a shaft with a plurality of staples disposed therein. The staple shaft assembly can include a staple advancing and forming assembly. The system can further include a drive system operably coupled between at least one motor and the staple advancing and forming assembly. The system can further include a control system configured to operably couple to the at least one motor. The control system can be configured to actuate the at least one motor to thereby control actuation of the drive system, as opposed to manual actuation via a trigger or other actuated mechanism, and can enable controlled movement of the staple advancing and forming assembly during use of the surgical stapler. In an exemplary embodiment, the control system is configured to modify a force being applied to the drive system by the at least one motor based at least in part on a predetermined threshold, such as a predetermined motor force threshold.

An exemplary surgical stapling system can include a variety of features as described herein and illustrated in the drawings. However, a person skilled in the art will appreciate that the surgical stapling systems can include only some of these features and/or it can include a variety of other features known in the art. The surgical stapling systems described herein are merely intended to represent certain exemplary embodiments. Moreover, while the drive and control systems are shown and described in connection with low profile staplers that sequentially deploys box staples, a person skilled in the art will appreciate that these systems can be used in connection with other surgical staples or surgical devices, such as forceps/graspers, needle drivers, scissors, electrocautery tools, clip appliers/removers, suction tools, irrigation tools, etc. Further, a person skilled in the art will appreciate that the surgical stapling systems described herein have application in conventional minimally-invasive and open surgical instrumentation as well as application in robotic-assisted surgery.

Surgical Stapling Device

Figure 2:
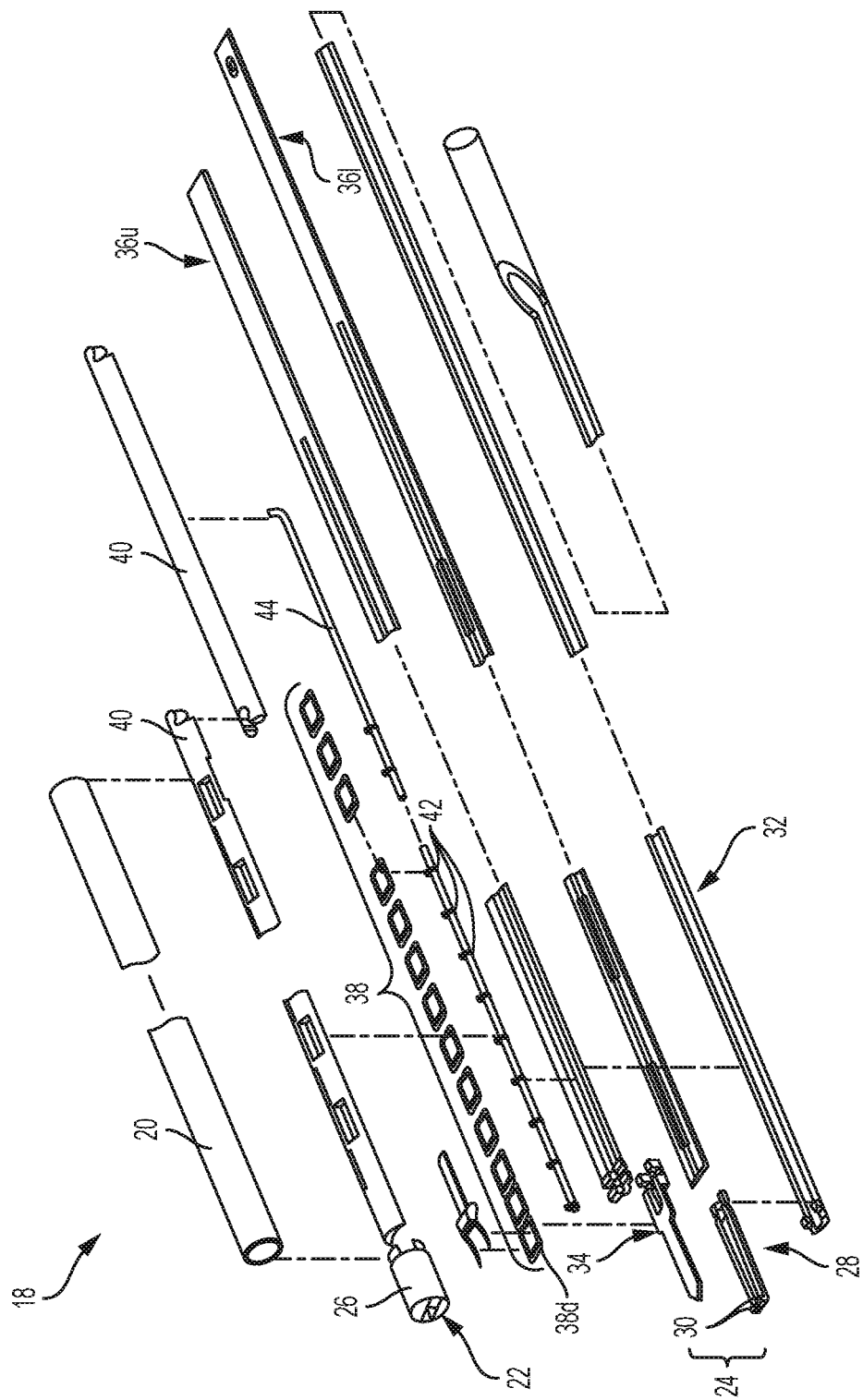
FIG. 2 is an exploded view of a distal portion of the surgical stapler of FIG. 1.

As indicated above, in an exemplary embodiment control systems are provided for controlling actuation of a surgical stapling device. FIGS. 1-2 illustrate one embodiment of a conventional surgical stapler 100 for use with a control system. As shown in FIG. 1, the surgical stapler 100 includes a housing 12 having a stationary handle 14 and a trigger actuator 16. The surgical stapler 100 also includes a staple shaft assembly 18 that includes an instrument shaft 20 that extends distally from the housing 12 for discharging staples from a distal deployment opening 22. The instrument shaft 20 can be rotated relative to the housing 12 via a rotation knob 23. The trigger 16 can facilitate both advancement of staples through the instrument shaft 20 and deployment of staples from the distal deployment opening 22. Further details on the housing 12, the stationary handle 14, and the trigger actuator 16 can be found in U.S. Pat. Nos. 8,469,252, 8,602,286, and 9,713,468, each of which is incorporated by reference herein in its entirety.

As shown in FIG. 2, the staple shaft assembly 18 can include a staple advancing assembly 24 extending through the instrument shaft 20 and a staple former 26 that is attached to a distal end 20*d* of the instrument shaft 20. The staple advancing assembly 24 and staple former 26 are collectively referred to herein as a staple advancing and forming assembly. As shown in FIG. 2, the staple advancing assembly 24 includes an anvil 28 having anvil tines 30 and being attached at a proximal end to an anvil extension 32. The staple advancing assembly 24 also includes a pusher 34 that extends substantially along an upper surface of the anvil 28. The pusher 34 is attached at a proximal end to upper and lower pusher extensions 36*u*, 36*l*. A stack of staples 38 in a closed configuration is disposed within the instrument shaft 20 between a staple guide 40 and the upper pusher extension 36*u*. An exemplary staple 38*d* in a closed configuration is shown in more detail in FIG. 3A. Staple advancers 42 are evenly spaced apart and extend along a rod 44 to help advance a distal-most staple 38*d* into a discharge channel during a staple deployment sequence. A shoe flexibly extends from the distal end of the staple guide 40 for indexing a single, distal-most staple 38*d* in the stack 38 into a staging position within the discharge channel and on the anvil 28 during each deployment sequence.

In use, actuation of the trigger 16 allows the anvil 28 to move proximally into the distal deployment opening 22 against the pusher 34. Further actuation of the trigger 16 allows the anvil 28 and the pusher 34 to move together further proximally. During this motion, the anvil 28 stops moving proximally, and the pusher 34 continues to a location even further proximally, thereby forming the discharge channel and allowing the shoe to index the distal-most staple 38*d* from the stack 38 into a staging position within the discharge channel. The pusher 34 then moves distally through the discharge channel, advancing against the back span 50 of the staple 38d to pin the staple 38d against the anvil 28. Once the pusher 34 has pinned the staple 38d against the anvil 28, the pusher 34 and the anvil 28 move distally together until the staple 38d extends through the distal deployment opening 22 and the anvil 28 reaches a stop, thereby preventing further distal movement of the anvil 28. After the anvil 28 has reached its distal-most position, the pusher 34 continues to move further distally to move the staple 38d from its closed configuration to an open configuration, which is shown in more detail in FIG. 3B. As such, the pusher 34 further acts as a spreader for opening the staple 38d.

The pusher 34 opens the staple 38d by applying a distally directed force to the staple back span 50 while the staple 38d is pinned against anvil tines 30. The force of the pusher 34 is applied to a mid-section of the back span 50, while the back span 50 is held fixed at the intersections between the back span 50 and staple legs 52, 54 by the anvil tines 30. As the pusher 34 continues to move distally, the staple 38d is expanded open as its legs 52, 54 are pulled outward by the force of the pusher 34 against the opposite fixed forces at the leg intersections and the lateral motion of the anvil tines 30. This lateral motion is caused by the continued distal motion of the pusher 34 relative to the fixed distal-most location of the anvil 28. This results in substantially simultaneously causing an indentation to be formed in the center of the staple back span 50.

Once the opened staple 38d (FIG. 3B) is positioned around or into the tissue, the trigger 16 is further actuated to move the staple former 26 to its distal-most position to form the staple 38d into a tissue-engaging configuration, which is shown in more detail in FIG. 3C. The trigger 16 is then released causing the staple former 26 and the pusher 34 to proximally retract and move out of engagement with the staple 38d, thereby releasing the staple 38d. Once the pusher 34 comes into contact with anvil 28, they both proximally retract. After the anvil 28 retracts to its home position, the pusher 34 continues to proximally retract to its home position. Once the pusher 34 has reached its home position, another deployment sequence can be initiated.

Additional details on surgical staplers, such as the conventional surgical stapler described above, are disclosed in U.S. Pat. Nos. 8,469,252, 8,602,286, 9,713,468, and 9,713,471 each of which is incorporated herein by reference in its entirety.

As discussed above, a user applies manual force to the trigger 16 in order to drive the staple shaft assembly 18 so to deploy the distal-most staple 38d about or into tissue. As such, the surgical stapler 100, as illustrated in FIGS. 1-2, is a manually-operated device. However, more and more surgical procedures are being performed using electrically-powered surgical devices that are either hand-held or that are coupled to a surgical robotic system. Unlike manually-operated devices, electrically-powered surgical devices can lack control and tactile feedback, thereby reducing a surgeon's ability to effectively, accurately, and safely use these devices. Further, manually-operated devices are typically displacement controlled in which mechanical hard stops are used to allow the device to shift to different stages of operation, for example, from advancement to formation of a staple. However, using mechanical stops in an electrically-powered device has its disadvantages. For example, a user can be limited in assessing whether a jam has occurred in the device or if the staple has been prematurely dislodged from the device during use.

Accordingly various embodiments of drive and control systems are provided for producing real-time feedback during the operation of electrically-powered surgical devices so as to enable a surgeon or other user to effectively and accurately use such devices. In general, the drive system is operably coupled between at least one motor and at least one drive assembly, such as the staple advancing and forming assembly. The control system is operably coupled to the at least one motor and is configured to actuate the at least motor to drive the drive system and thereby control movement of the staple advancing and forming assembly.

Motors/Drive System

In general, one or more motors can be used to drive various surgical device functions. The device functions can vary based on the particular type of surgical device, but in general a surgical device can include one or more drive systems that can be configured to cause a particular action or motion to occur, such as shaft and/or end effector rotation, end effector articulation, jaw opening and/or closing, firing to deliver an implantable component such as a clip, staple, adjunct, etc., energy delivery, etc. An exemplary drive system is shown in FIG. 4B and discussed in more detail below. Each drive system can include various components, such as one or more gears that receive a rotational force from the motor(s) and that transfer the rotational force to one or more drive shafts to cause rotary or linear motion of the drive shaft(s). For example, with reference to the drive system 257 that is discussed in more detail below, one or more motors can be coupled through the drive system to one or more drive assemblies to thereby advance the pusher, the anvil, and/or the staple former. The motor(s) can be located within the surgical device itself or, in the alternative, coupled to the surgical device such as via a robotic surgical system. Each motor can include a rotary motor shaft that is configured to couple to the one or more drive systems of the surgical device so that the motor can actuate the drive system(s) to cause a variety of movements and actions of the device.

It should be noted that any number of motors can be used for driving any one or more drive systems on a surgical device. For example, one motor can be used to actuate two different drive systems for causing different motions. Moreover, in certain embodiments, the drive system can include a shift assembly for shifting the drive system between different modes for causing different actions. A single motor can in other aspects be coupled to a single drive assembly. A surgical device can include any number of drive systems and any number of motors for actuating the various drive systems. The motor(s) can be powered using various techniques, such as by a battery on the device or by a power source connected directly to the device or connected through a robotic surgical system.

Additional components, such as sensors or meter devices, can be directly or indirectly coupled to the motor(s) in order to determine and/or monitor at least one of displacement of a drive system coupled to the motor or a force on the motor during actuation of the drive system. For example, a rotary encoder can be coupled to the motor to monitor the rotational position of the motor, thereby monitoring a rotational or linear movement of a respective drive system coupled to the motor. Alternatively or in addition, a torque sensor can be coupled to the motor to determine or monitor an amount of force being applied to the motor during device operation. It is also contemplated that other ways to determine or monitor force on the motor can include (i) measuring current though the motor by using a sensor or a meter device; or (ii) measuring differences between actual velocity of the motor or components, which may include a combination of a distance travelled and an expired time, and the commanded velocity.

In certain embodiments, when the at least one motor is activated, its corresponding rotary motor shaft drives the rotation of at least one corresponding gear assembly located within the drive system of the surgical device. The corresponding gear assembly can be coupled to at least one corresponding drive shaft, thereby causing linear and/or rotational movement of the at least corresponding drive shaft. While movement of two or more drive shafts can overlap during different stages of operation of the drive system, each motor can be activated independently from each other such that movement of each corresponding drive shaft does not necessarily occur at the same time or during the same stage of operation.

When the at least one drive shaft is being driven by its corresponding motor, a rotary encoder, if used, can determine the rotational position of the motor, thereby indicating linear or rotational displacement of the at least one drive shaft. Additionally or in the alternative, when the corresponding motor is activated, the torque sensor, if used, can determine the force on the motor during linear or rotary movement of the at least one drive shaft.

As indicated above, the motors as well as the control system can be disposed within the handle housing, like housing 12 shown in FIG. 1, or can be located outside of the handle housing, such as within a surgical robotic system. Over the years a variety of minimally invasive robotic (or "telesurgical") systems have been developed to increase surgical dexterity as well as to permit a surgeon to operate on a patient in an intuitive manner. Many of such systems are disclosed in the following U.S. Patents, which are each herein incorporated by reference in their respective entirety: U.S. Pat. No. 5,792,135 entitled "Articulated Surgical Instrument For Performing Minimally Invasive Surgery With Enhanced Dexterity and Sensitivity," U.S. Pat. No. 6,132,368 entitled "Multi-Component Telepresence System and Method," U.S. Pat. No. 6,231,565 entitled "Robotic Arm DLUS For Performing Surgical Tasks," U.S. Pat. No. 6,783,524 entitled "Robotic Surgical Tool With Ultrasound Cauterizing and Cutting Instrument," U.S. Pat. No. 6,364,888 entitled "Alignment of Master and Slave In a Minimally Invasive Surgical Apparatus," U.S. Pat. No. 7,524,320 entitled "Mechanical Actuator Interface System For Robotic Surgical Tools," U.S. Pat. No. 7,691,098 entitled "Platform Link Wrist Mechanism," U.S. Pat. No. 7,806,891 entitled "Repositioning and Reorientation of Master/Slave Relationship in Minimally Invasive Telesurgery," and U.S. Pat. No. 7,824,401 entitled "Surgical Tool With Wristed Monopolar Electrosurgical End Effectors." Many of such systems, however, have in the past been unable to generate the magnitude of forces required to effectively cut and fasten tissue.

Figure 4A:
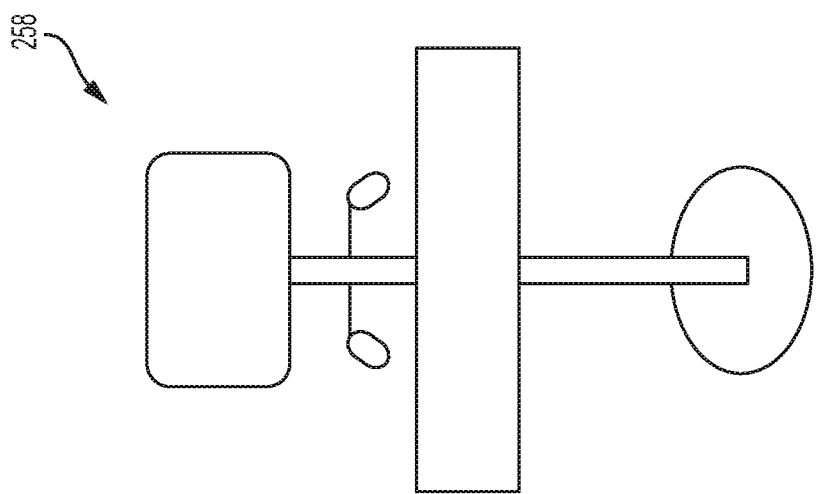
FIG. 4A is a perspective view of an exemplary embodiment of a surgical robotic system that includes a robotic arm having a drive system mounted in a motor housing on an end of the robotic arm, and being wirelessly coupled to a control system.
Figure 4A:
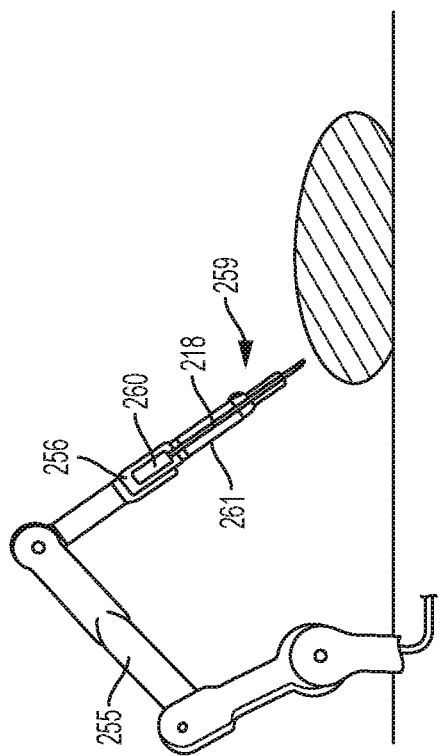
Figure 4B:
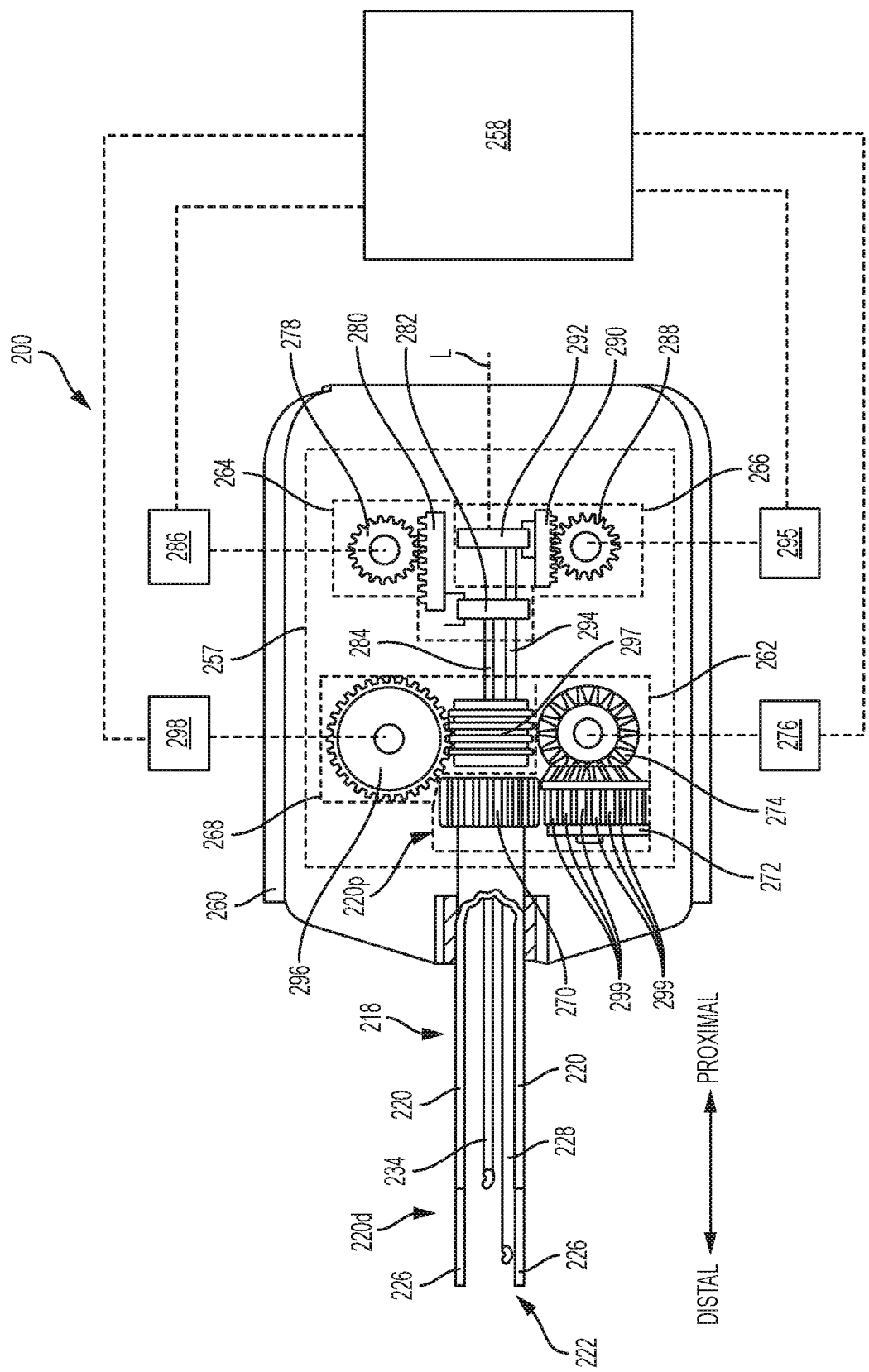
FIG. 4B is a side, partially transparent schematic view of an exemplary surgical stapling system having a staple shaft assembly that is coupled to a drive system, the drive system being coupled to motors that are operably coupled to a control system.

For example, FIG. 4A illustrates a robotic arm 255 wirelessly coupled to a control system 258 having a console with a display and two user input devices. One or more motors (not shown) are disposed within a motor housing 256 that is coupled to an end of the robotic arm 255. A tool or drive system housing 260 on a surgical tool can house a drive system (not shown) and it can be mounted to the motor housing 256 to thereby operably couple the motor(s) to the drive system. As a result, when the motors are activated by the control system, the motor(s) can actuate the drive system. As shown in FIG. 4A, a staple shaft assembly 218 extends from the tool housing 260. During surgery, the staple shaft assembly 218 can be placed within and extend through a trocar 259 that is mounted on the bottom of a carrier 261 extending between the motor housing 256 and a trocar support. The carrier 261 allows the tool to be translated into and out of the trocar 259.

Various wireless communication embodiments are described in U.S. patent application Ser. No. 13/118,259 to James R. Giordano et al. filed on May 27, 2011, the disclosure of which is herein incorporated by reference in its entirety.

FIG. 4B illustrates an exemplary embodiment of surgical stapling system 200 having a tool housing 260 containing a drive system 257 and being coupled to a proximal end 220$p$ of an instrument shaft 220 of a staple shaft assembly 218. The drive system 257 is shown coupled to motors 276, 286, 295, 298 that are operably coupled to a control system 258. A person skilled in the art will appreciate that the motors and control system can be located within the tool housing 260 to form a powered hand-held device, or they can be located external of the housing 260, such as in a robotic system as described with respect to FIG. 4A. Moreover, aside from the differences described in detail below, the staple shaft assembly 218 can be similar to staple shaft assembly 18 of FIGS. 1-2 and is therefore not described in detail herein. Further, for purposes of simplicity, certain components of the staple shaft assembly 218 are not illustrated in FIG. 4B.

While the drive system 257 can have a variety of configurations, in this exemplary embodiment, the drive system 257 includes gearing assemblies that are part of four drive assemblies: a shaft rotation drive assembly 262 configured to cause the instrument shaft 220 to rotate about the longitudinal axis L of the staple shaft assembly 218; a pusher drive assembly 264 configured to cause the pusher 234 to advance in distal and proximal directions relative to the housing 260; an anvil drive assembly 266 configured to cause the anvil 228 to advance in distal and proximal directions relative to the housing 260; and a staple former drive assembly 268 configured to cause the instrument shaft 220, and consequently, the stapler former 226, to advance in the distal and proximal directions relative to the housing 260. Each drive assembly, as well as the gearing in the drive system for driving the drive assemblies, is discussed in more detail below. Each gearing assembly in the drive system can be coupled to a rotary motor shaft of a corresponding motor, which in the illustrated embodiment (FIG. 4A) is disposed in a driving system housing 260 on the end of the robotic arm 255. During actuation, the corresponding motor can actuate the drive system to thereby actuate the drive assemblies. Further, as described above, one or more motors can be coupled to a corresponding rotary encoder that provides displacement information to the control system 258 for at least one of the pusher 234, the anvil 228, and the staple former 226, during operation of the drive system 257. Alternatively or in addition, the one or more motors can be coupled to a corresponding torque sensor that provides the control system 258 with information about the amount of force being applied to the motor(s) during operation of the drive system 257.

Exemplary motors for use with the systems disclosed herein are described, for example, in U.S. Pat. Nos. 9,445,816 and 9,585,658 and in U.S. Patent Publication Nos. 2012/0292367, 2013/0325034, and 2015/0209059.

Shaft Rotation Drive Assembly

While the shaft rotation drive assembly 262 can have a variety of configuration, in some implementations, the shaft rotation drive assembly 262, as shown FIG. 4B, can include a tube gear segment 270 that is formed on (or attached to) a proximal end 220$p$ of the instrument shaft 218 for operable engagement with a rotational gear assembly. As shown, the rotational gear assembly can include a rotary drive gear 272 that is in meshing engaging with the tube gear segment 270. The rotational gear assembly can also include a rotation drive gear 274 that is operably coupled to a shaft motor 276. The aforementioned gears of the drive system are thus coupled between motor 276 and the instrument shaft 220. In use, when the shaft motor 276 is activated, its corresponding rotary motor shaft drives the rotation of the rotational gear assembly, and consequently the tube gear segment 270, thereby causing the rotation of the instrument shaft 220. It will be appreciated that the application of a rotary output motion from the shaft motor 276 in one direction will result in the rotation of the instrument shaft 220 about the longitudinal axis L in a first direction and an application of the rotary output motion in an opposite direction will result in the rotation of the instrument shaft 220 in a second direction that is opposite to the first direction.

Pusher Drive Assembly

The pusher drive assembly 264 can have a variety of configurations. For example, as shown in FIG. 4B, the pusher drive assembly 264 can include a rotary drive gear 278 that is in meshing engagement with a rack 280 that is coupled to a drive bracket 282 having a drive shaft 284 extending therefrom and in contact with the proximal end of the pusher 234. The rotary drive gear 278 can be operably coupled to a pusher motor 286. The aforementioned gears of the drive system are thus coupled between motor 286 and the pusher 234. In use, when the pusher motor 286 is activated by the control system 258, its corresponding rotary motor shaft drives the rotation of the rotary drive gear 278, thereby causing linear movement of the pusher 234. It will be appreciated that the application of a rotary output motion from the pusher motor 286 in one direction will result in the linear movement of the pusher 234 in a distal direction to advance the distal-most staple, like the distal-most staple 38*d* shown in FIG. 2, though the distal deployment opening 222 and move the distal-most staple, like distal-most staple 38*d*, from the closed configuration (FIG. 3A) to the open configuration (FIG. 3B). Further, application of the rotary output motion in an opposite direction will result in the linear movement of the pusher 234 in a proximal direction to retract the pusher 234 to release the distal-most staple and return the pusher 234 to its initial position.

Anvil Drive Assembly

While the anvil drive assembly 266 can have a variety of configurations, in some embodiments, as shown in FIG. 4B, the anvil drive assembly 266 can include a rotary drive gear 288 that is in meshing engagement with a rack 290 that is coupled to a drive bracket 292 having a drive shaft 294 extending therefrom and in contact with the proximal end of the anvil 228. The rotary drive gear 288 can be operably coupled to an anvil motor 295. The aforementioned gears of the drive system are thus coupled between motor 295 and the anvil 228. In use, when the anvil motor 295 is activated by the control system 258, its corresponding rotary motor shaft drives the rotation of the rotary drive gear 288, thereby causing linear movement of the anvil 228. It will be appreciated that the application of a rotary output motion from the motor in one direction will result in the linear movement of the anvil 228 in a distal direction to advance the distal-most staple, like distal-most staple 38*d* shown in FIG. 2, through the discharge deployment opening 222 of the staple shaft assembly 218. The anvil 228 and pusher 234 distally advance together to advance the distal-most staple, like distal-most staple 38*d*. Further, application of the rotary output motion in an opposite direction will result in the linear movement of the anvil 228 in a proximal direction to retract the anvil 228 to its initial position.

Staple Former Drive Assembly

The staple former drive assembly 268 can have a variety of configurations. For example, as shown in FIG. 4B, the staple former drive assembly 268 can include a rotary drive gear 296 that is in meshing engagement with a circumferential rack 297 formed on (or attached to) the proximal end 220*p* of the instrument shaft 220. While the circumferential rack 297 is shown to be positioned further proximal relative to the tube gear segment 270, it is also contemplated that the circumferential rack 297 can be positioned on (or to) other sections of the instrument shaft 220. The rotary drive gear 296 can be operably coupled to a staple former motor 298. The aforementioned gears of the drive system are thus coupled between motor 298 and the staple former 226. In use, when the staple former motor 298 is activated by the control system 258, its corresponding rotary motor shaft drives the rotation of the rotary drive gear 296, which causes linear movement of the instrument shaft 220, and consequently, the staple former 226. It will be appreciated that the application of a rotary output motion from the staple former motor 298 in one direction will result in the linear movement of the instrument shaft 220, and thus the staple former 226, in a distal direction such that the staple former 226 moves the distal-most staple, like distal-most staple 38*d* shown in FIG. 2, from the open configuration (FIG. 3B) to the tissue-engaging configuration (FIG. 3C). Further, application of the rotary output motion in an opposite direction will result in the linear movement of the instrument shaft 220 and staple former 226 in a proximal direction to release the distal-most staple, like distal-most staple 38*d*, in the tissue-engaging configuration, from the staple shaft assembly 218 and retract the instrument shaft 218 and staple former 226 to their initial position. It is also contemplated that the instrument shaft 218 can function as the staple former 226, and therefore, in some embodiments, the staple former 226 can be omitted from surgical stapling systems described herein.

It should be noted that in some embodiments, the longitudinal slots 299 of the rotary drive gear 272 of the shaft rotation drive assembly 262 can have a length that is equal to or greater than the amount of linear distance the instrument shaft 220 can move in a distal direction. As a result, the tube gear segment 270 can slide along the elongated longitudinal slots 299, during linear movement of the instrument shaft 220 without disengagement from the rotary drive gear 272. In another embodiment, the tube gear segment 270 can be engaged with longitudinal slots extending at least partially along the outer surface of the instrument shaft 220 such that the tube gear segment 270 can slide along the instrument shaft 220 when the instrument shaft 220 moves in distal and proximal directions. In such an embodiment, the rotational gear assembly can also be positioned on a longitudinal shaft that is co-linear with the instrument shaft 220 to allow the rotational gear assembly to correspondingly slide with the tube gear segment 270 so that the tube gear segment 270 and the rotational gear assembly can remain engaged. It is also contemplated that other sliding mechanisms/assemblies can be used to allow corresponding linear movement of at least the tube gear segment 270 with that of the instrument shaft 220.

Stages of Operation

In use, the drive system can have one or more stages of operation. In general, the control system actuates one or more motors for driving movement/action of the drive system for each stage of operation of the drive system. That is, during each stage of operation the control system activates one or more motors to drive the drive system and thereby drive the corresponding one or more drive assemblies to effect a rotation and/or linear movement of particular elements of the staple shaft assembly, such as the instrument shaft, the pusher, the anvil, and/or the staple former, as described below. Thus, movement of the drive system during different stages of operation is controlled by the control system and the operation of the control system will be discussed in more detail below.

Figure 5:
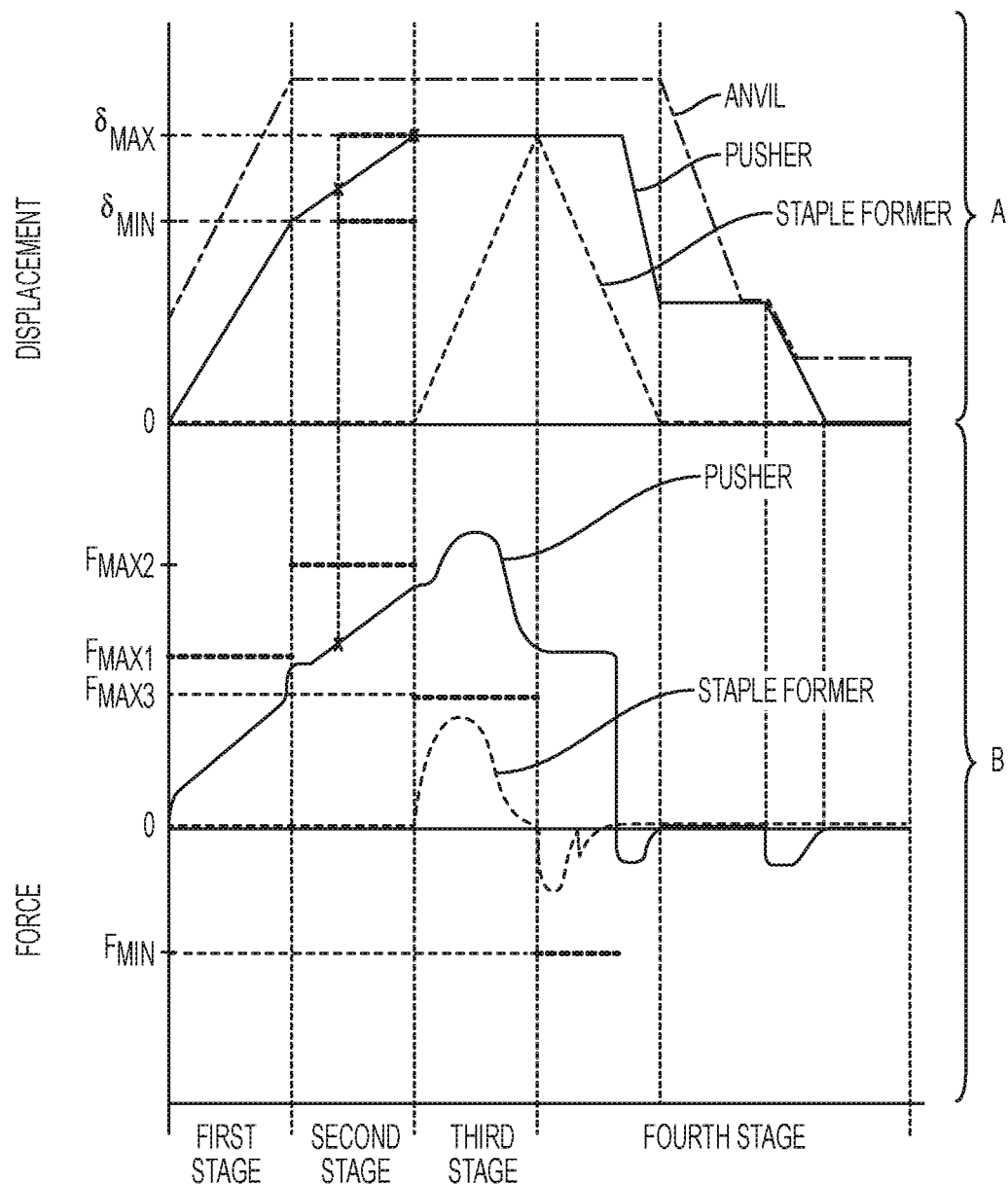
FIG. 5 is a graph illustrating the displacement of the pusher, the anvil, and the staple former of the staple shaft assembly shown in FIGS. 4A and 4B during actuation of the drive system, and a process for controlling the motor force being applied to the pusher, the anvil, and the staple former shown in FIGS. 4A and 4B during actuation of the drive system.

FIG. 5 illustrates four stages of operation of the drive system, and in particular section A of FIG. 5 illustrates displacement of each of the anvil, pusher, and stapler former during each stage of operation. Section B of FIG. 5 illustrates a measured force required to move each of the anvil, pusher, and staple former during each stage of operation, as well as various threshold forces. Section B of FIG. 5 will be discussed in more detail below in connection with the operation of the control system.

During the first stage of operation, the pusher motor 286 can be activated by the control system 258, causing the rotary motor shaft to drive the pusher drive assembly 264 to distally move the pusher 234 from a proximal position to an intermediate position. Further, during the first stage of operation, the anvil motor 295 can be activated, by the control system 258, causing the rotary motor shaft to drive the anvil drive assembly 266 to distally move the anvil 228 from a proximal position to a distal-most position. In certain embodiments, actuation of the anvil motor 295 and the pusher motor 286 can at least partially overlap such that the anvil 228 and the pusher 234 can concurrently move in a distal direction for at least a portion of the first stage of operation. In one embodiment, the anvil 228 and pusher 234 concurrently move in a distal direction for the entire first stage of operation. The distal movement of the anvil 228 and the pusher 234 during this first stage of operation is shown in section A of FIG. 5. This movement causes the distal-most staple, like distal-most clip 38d in FIG. 2, to advance into the discharge channel and through the distal deployment opening at the distal end 220d of the instrument shaft 220.

Once the anvil 228 reaches its distal-most position, the anvil motor 295 is deactivated by the control system 258, and the second stage of operation can begin. During the second stage of operation, the pusher drive assembly 264 continues to drive the pusher 234 from the intermediate position to a distal-most position such that the distal-most staple, like distal-most staple 38d, can move from the closed configuration (FIG. 3A) to the open configuration (FIG. 3B). The further distal movement of the pusher 234 during this second stage of operation is shown in section A of FIG. 5. After the distal-most staple is in the open configuration, the pusher motor 286 is deactivated by the control system 258, and the third stage of operation can start.

In certain embodiments, it may be desirable to partially open the distal-most staple such that the distal-most staple is opened to a secondary open configuration. This secondary open configuration can be effected by ceasing motor movement, by the control system 258, before the pusher 234 is driven to its maximum displacement threshold, $\delta_{MAX}$ as shown in section A of FIG. 5. That is, the control system 258 can deactivate the pusher motor 286 such that the pusher 234 is distally driven from the intermediate position to a secondary intermediate position effecting a displacement between the minimum and maximum displacement thresholds $\delta_{MIN}$, $\delta_{MAX}$ of the pusher 234 shown in FIG. 5A, thereby preventing the distal-most staple from fully expanding to the open configuration.

During the third stage of operation, the staple former motor 298 can be activated, by the control system 258, causing the rotary motor shaft to drive the staple former drive assembly 268 to distally move the staple former 226 from a proximal position to a distal-most position. This distal movement of the staple former 226 during this stage of operation is shown section A in FIG. 5. This movement results in forming the distal-most staple around tissue. That is, during this third stage of operation, the staple former 226 moves the distal-most staple, like distal-most staple 38d, from the open configuration (FIG. 3B) to the tissue-engaging configuration (FIG. 3C). It should be noted that when the distal-most staple is moved from the closed position to the secondary open configuration, as discussed above, the staple former 226 moves the staple from the secondary open configuration to a secondary tissue-engaging configuration.

In some embodiments, once the staple is moved into the tissue-engaging configuration (or secondary tissue-engaging configuration), the drive system 257 can begin a fourth stage of operation, as shown in section A of FIG. 5, in which the staple former motor 298, the pusher motor 286, and the anvil motor 295 can be activated and the corresponding rotary motor shafts can proximally retract the staple former 226, the pusher 234, and the anvil 228, respectively, to their initial positions to release the staple from the instrument shaft 220 and to allow for the subsequent distal-most staple to advance into the discharge channel and on the anvil 228 for the next deployment sequence. As shown in section A of FIG. 5, during different portions of the fourth stage of operation, there is overlapping proximal movement between the staple former 226 and the pusher 234 and between the pusher 234 and the anvil 228.

In some embodiments, the actuation of the shaft rotation drive assembly 262 can be effected by the control system 258 during any of the foregoing stages of operation such that the activation of the shaft rotation drive assembly 262 can overlap with the pusher drive assembly 264, the anvil drive assembly 266, and/or the staple former drive assembly 268. In other embodiments, the shaft rotation drive assembly 262 can be actuated during a separate stage of operation of the drive system 257 and can occur before or after any of the foregoing stages of operation described herein.

Operation of Control System

Generally, as discussed above, the control system can control movement and actuation of a surgical device. For example, the control system can include at least one computer system and can be operably coupled to the at least one motor that drives a drive system on the surgical device. The computer system can include components, such as a processor, that are configured for running one or more logic functions, such as with respect to a program stored in a memory coupled to the processor. For example, the processor can be coupled to one or more wireless or wired user input devices ("UIDs"), and it can be configured for receiving sensed information, aggregating it, and computing outputs based at least in part on the sensed information. These outputs can be transmitted to the drive system of surgical device to control the surgical device during use.

In certain embodiments, the control system can be a closed-loop feedback system. The stored data within the computer system can include predetermined threshold(s) for one or more stages of operation of the drive system. When the control system is actuated, it drives one or more motors on or coupled to the surgical device, consequently actuating the drive system through each stage of operation. During each stage of operation, the control system can receive feedback input from one or more sensors coupled to the motor(s) that sense displacement and/or torque of the motor(s). The computer system can aggregate the received feedback input(s), perform any necessary calculations, compare it to the predetermined threshold for the corresponding stage of operation, and provide output data to the motor(s). If at any time during each stage of operation the control system determines that the received input exceeds a maximum predetermined threshold or is less than a minimum predetermined threshold, the control system can modify the output data sent to the motor based on the programmed logic functions. For example, the control system can modify the output data sent to the motor(s) to reduce a current delivered to the motor to reduce motor force or a voltage delivered to the motor to thereby reduce a rotational speed of the motor(s) or to stop movement of the motor(s).

Referring back to FIGS. 4A and 4B, the control system 258, which includes at least one computer system, can be operably coupled (wired or wirelessly) to each of the motors 276, 286, 295, 298 that drive the various components of the drive system 257. Various wireless communication embodiments are described in U.S. patent application Ser. No. 13/118,259 to James R. Giordano et al. filed on May 27, 2011, the disclosure of which is herein incorporated by reference in its entirety. As described above, for each stage of operation one or more motors 276, 286, 295, 298 are actuated by the control system 258. As a result, the control system 258 can control the movement of at least one of the instrument shaft 220, the pusher 234, the anvil 228, and the staple former 226. In particular, the control system 258 can monitor a force required to move each of the anvil, pusher, and staple former during each stage of operation, can compare the monitored force to various threshold forces, and can modify or terminate current applied to the motor to modify or terminate the motor force or can modify or terminate voltage applied to the motor to thereby modify or terminate movement of the anvil, pusher, and/or staple former.

For example, in one embodiment, as shown in section B of FIG. 5, for each stage of operation there can be at least one predetermined motor force threshold. As shown, the predetermined motor force thresholds in the first and second stages of operation, $F_{MAX1}$ and $F_{MAX2}$, respectively, are based at least in part on the motor force applied to the pusher 234, and the predetermined motor force thresholds in the third and fourth stages of operation are based at least in part on the motor force applied to the staple former 226, $F_{MAX3}$ and $F_{MIN}$, respectively. The predetermined motor force thresholds in each of the first, second, and third stages are maximum force thresholds, whereas the predetermined motor force threshold in the fourth stage of operation is a minimum motor force threshold. For each stage of operation, the predetermined motor force threshold(s) for the pusher 234 and the staple former 226 and the desired displacement for the pusher 234, the anvil 228, and the staple former 226 are stored as data in the computer. While the control system 258 can be designed to control various operations, in this exemplary embodiment, for each stage of operation the control system 258 actuates one or more motor(s) to move particular elements a known distance, as indicated by the displacement shown in section A of FIG. 5, while also measuring the force.

In the first stage of operation, the control system 258 can actuate and control the pusher and anvil motors 286, 295 to distally move the pusher 234 and anvil 228, respectively, known distances (as shown in section A of FIG. 5). The control system 258 can concurrently receive real-time feedback data from a torque sensor on the pusher motor 286. If at any time during this stage of operation the control system 258 determines that the force applied by the pusher motor 286 exceeds the maximum predetermined threshold, $F_{max1}$ in section B of FIG. 5, the control system 258 can modify the output data sent to the pusher motor 286 to cease movement (or in the alternative, reduce current to the motor to reduce motor force or reduce voltage to the motor to reduce motor speed). In one embodiment, this maximum predetermined threshold $F_{max1}$ correlates to feeding a staple into the discharge channel, and therefore exceeding this threshold during the first stage of operation can be indicative of an improper feeding of the staple and/or a jam. Certain forces are required to feed a staple into the discharge channel during normal operation and the range of these forces can be determined during manufacturing. The maximum force threshold $F_{max1}$ can therefore be set at a maximum force that could be applied for properly feeding the staple during normal operation.

In the second stage of operation, the control system 258 can continue to actuate and control the pusher motor 286 to distally move the pusher 234 to a further distal known distance and can concurrently receive real-time feedback data from the torque sensor on the pusher motor 286. If at any time during this stage of operation the control system 258 determines that the force applied by the pusher motor 286 exceeds the maximum predetermined threshold, $F_{max2}$ in section B of FIG. 5, the control system 258 can modify the output data sent to the pusher motor 286 to cease movement (or in the alternative, reduce current to the motor to reduce motor force or reduce voltage to the motor to reduce motor speed). In one embodiment, this maximum predetermined force threshold $F_{max2}$ correlates to the opening of the staple, and therefore exceeding this threshold during the second stage of operation can be indicative of improper opening of the staple and/or a jam. Certain forces are required to move a staple from the closed configuration to the open configuration during normal operation. A range of suitable forces can be determined during manufacturing, and therefore the maximum force threshold $F_{max2}$ can be set at the maximum force that could be applied to properly open the staple during normal operation.

Further, during this second stage of operation, the control system 258 can also receive real-time feedback data from the rotary encoder on the pusher motor 286 to indicate the displacement of the pusher 234. If at any time during this stage of operation the control system 258 determines that the pusher displacement has not reached or exceeded the minimum displacement threshold, $\delta_{MIN}$ in section A of FIG. 5, the control system 258 can modify the force being applied to the pusher driver assembly 264. In one embodiment, this minimum predetermined displacement threshold $\delta_{MIN}$ correlates to the security of the staple, and therefore failing to meet this threshold during this stage of operation can be indicative of premature staple dislodgment from the stapling device. To properly open the staple, the pusher is required to advance a minimum distance. A range of suitable minimum distances can be determined during manufacturing, and therefore the minimum displacement threshold $\delta_{MIN}$ can be set at the smallest determined distance required to properly open the staple during normal operation.

Similarly, if at any time during this second stage of operation, the control system 258 determines that the pusher displacement has exceeded the maximum displacement threshold, $\delta_{MAX}$ in section A of FIG. 5, the control system 258 can modify the force being applied to the pusher motor 286. In one embodiment, this maximum predetermined displacement threshold $\delta_{MAX}$ correlates to the opening of the staple, and therefore meeting this threshold during this stage of operation can be indicative of proper opening of the staple, whereas exceeding this threshold can be indicative of improperly opening of the staple, e.g. over-extended. To properly open the staple to its max open configuration (FIG. 3C), the pusher is required to advance a maximum distance. A range of suitable distances can be determined during manufacturing, and therefore the maximum displacement threshold $\delta_{MAX}$ can be set at the greatest determined distance required to properly open the staple during normal operation.

In the third stage of operation, the control system 258 can actuate and control the staple former motor 298 to distally move the staple former 226 a known distance and can concurrently receive real-time feedback data from the torque sensor on the staple former motor 298. If at any time during this stage of operation the control system 258 determines that the force applied by the staple former motor 298 exceeds the maximum predetermined threshold, $F_{max3}$ in section B of FIG. 5, the control system 258 can modify the output data sent to the staple former motor 298 to cease movement (or in the alternative, reduce current to the motor to reduce motor force or reduce voltage to the motor to reduce motor speed). In one embodiment, this maximum predetermined force threshold $F_{max3}$ correlates to the forming of the staple around tissue, and therefore exceeding this threshold during this stage of operation can be indicative of improper formation of the staple about tissue and/or a jam. Certain forces are required to form the open staple about tissue during normal operation. A range of suitable forces can be determined during manufacturing, and therefore the maximum force threshold $F_{max3}$ can be set at the maximum force that could be applied to properly form the staple around tissue, i.e., into its tissue-engaging configuration, during normal operation.

In the fourth stage of operation, the control system 258 can actuate and control the staple former motor 298 to proximally move the staple former 226 to a second known distance and can concurrently receive real-time feedback data from the torque sensor on the staple former motor 298. If at any time during this stage of operation the control system 258 determines that the force applied by the staple former motor 298 falls below the minimum predetermined threshold, $F_{min}$ in section B of FIG. 5, the control system 258 can modify the output data sent to the staple former motor 298 to cease movement (or in the alternative, reduce current to the motor to reduce motor force or reduce voltage to the motor to reduce motor speed). In one embodiment, this minimum predetermined force threshold $F_{min}$ correlates to the release of the staple, and therefore failing to meet or exceed this threshold during this stage of operation can be indicative of an improper release of the staple and/or a jam. Certain forces are required to properly release the staple from the staple shaft assembly during normal operation. A range of suitable forces for retracting the staple former to release the staple can be determined during manufacturing, and therefore the minimum force threshold $F_{min}$ can be set at the minimum amount of force required to properly release the staple during normal operation. It should be noted that during this stage of operation, the control system 258 can also actuate and control the pusher and anvil motors 286, 295 to proximally move the pusher 234 and anvil 228, respectively, to second known distances.

In other embodiments, mechanical stops can be used to control displacement of the pusher, the anvil, and the staple former during each stage of operation. That is, rather programming the computer system with displacement data, as described above, one or more mechanical stops can be used to control displacement during each stage of operation. Thus, the control system can modify the output data sent to the motors to cease movement (or in the alternative, reduce current to the motor to reduce motor force or reduce voltage to the motor to reduce motor speed) when a mechanical stop is engaged (as would be indicated by a force spike) or the force applied by a motor exceeds a predetermined threshold.

In other embodiments, for each stage of operation, the control system can control the motion of the pusher, anvil, and/or stapler former until a predetermined motor force threshold(s) is met and can monitor the displacement based on predetermined displacement thresholds. For example, during each stage of operation, when the control system determines that the predetermined motor force threshold(s) have been met, the control system can then compare the displacement of the pusher, anvil and/or staple former against the predetermined displacement threshold(s) to determine whether the pusher, anvil, and/or staple former have moved the corresponding distance. In such instances, if the control system determines that the displacement of the pusher, anvil, and/or staple former fail to meet the predetermined displacement threshold(s), it can be indicative of an improper feeding, forming, releasing of the staple, and/or a jam. Further, during each stage of operation, if the control system determines that the predetermined displacement threshold(s) have been met prior to the predetermined motor force threshold(s), this can be indicative of improper feeding, forming, releasing of the staple and/or a jam. For each stage of operation, certain displacements of features are required to operate the device during normal operation. A range of suitable displacements can be determined during manufacturing. Thus, predetermined displacement thresholds can be used to determine whether the device is being operated properly during use.

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 6:
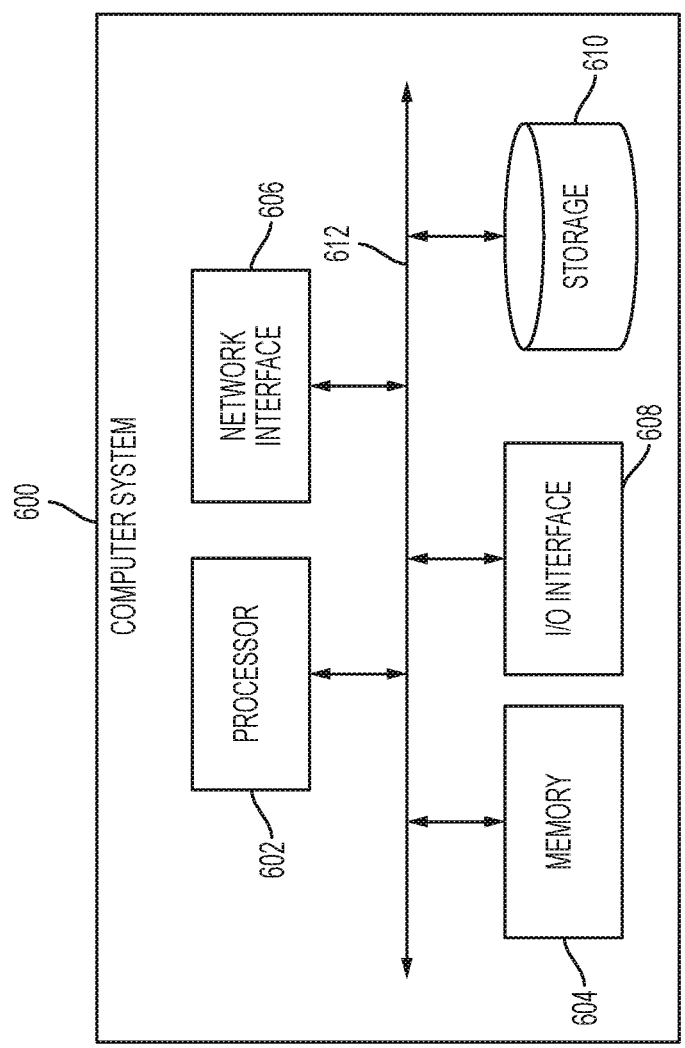
FIG. 6 illustrates one exemplary embodiment of a computer system that can be used to implement a control system of the present disclosure.

FIG. 6 illustrates one exemplary embodiment of a computer system 600. As shown, the computer system 600 includes one or more processors 602 which can control the operation of the computer system 600. "Processors" are also referred to herein as "controllers." The processor(s) 602 can include any type of microprocessor or central processing unit (CPU), including programmable general-purpose or special-purpose microprocessors and/or any one of a variety of proprietary or commercially available single or multi-processor systems. The computer system 600 can also include one or more memories 604, which can provide temporary storage for code to be executed by the processor(s) 602 or for data acquired from one or more users, storage devices, and/or databases. The memory 604 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 600 can be coupled to a bus system 612. The illustrated bus system 612 is an abstraction that represents any one or more separate physical busses, communication lines/interfaces, and/or multi-drop or point-to-point connections, connected by appropriate bridges, adapters, and/or controllers. The computer system 600 can also include one or more network interface(s) 606, one or more input/output (10) interface(s) 608 that can include one or more interface components, and one or more storage device(s) 610.

The network interface(s) 606 can enable the computer system 600 to communicate with remote devices, e.g., motor(s) coupled to the drive system 257 that is located within the surgical device or a robotic surgical system or other computer systems, over a network, and can be, for non-limiting example, remote desktop connection interfaces, Ethernet adapters, and/or other local area network (LAN) adapters. The IO interface(s) 608 can include one or more interface components to connect the computer system 600 with other electronic equipment, such as the sensors located on the motor(s). For non-limiting example, the IO interface(s) 608 can include high speed data ports, such as universal serial bus (USB) ports, 1394 ports, Wi-Fi, Bluetooth, etc. Additionally, the computer system 600 can be accessible to a human user, and thus the IO interface(s) 608 can include displays, speakers, keyboards, pointing devices, and/or various other video, audio, or alphanumeric interfaces. The storage device(s) 610 can include any conventional medium for storing data in a non-volatile and/or non-transient manner. The storage device(s) 610 can thus hold data and/or instructions in a persistent state, i.e., the value(s) are retained despite interruption of power to the computer system 600. The storage device(s) 610 can include one or more hard disk drives, flash drives, USB drives, optical drives, various media cards, diskettes, compact discs, and/or any combination thereof and can be directly connected to the computer system 600 or remotely connected thereto, such as over a network. In an exemplary embodiment, the storage device(s) 610 can include a tangible or non-transitory computer readable medium configured to store data, e.g., a hard disk drive, a flash drive, a USB drive, an optical drive, a media card, a diskette, a compact disc, etc.

The elements illustrated in FIG. 6 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 600 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 600 can also include a web server for generating and/or delivering the web pages to client computer systems.

In an exemplary embodiment, the computer system 600 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety. Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

What is claimed is:

1. A surgical stapling system, comprising:
    a staple shaft assembly having a shaft with a plurality of staples disposed therein in a closed configuration, the staple shaft assembly including a staple advancing and forming assembly;
    a drive system operably coupled between at least one motor and the staple advancing and forming assembly, the drive system having a plurality of stages of operation including a first stage of operation in which the drive system drives the staple advancing and forming assembly to advance a distal-most staple of the plurality of staples, a second stage of operation in which the drive system drives the staple advancing and forming assembly to move the distal-most staple from the closed configuration to an open configuration, and a third stage of operation in which the drive system drives the staple advancing and forming assembly to form the distal-most staple around tissue; and
    a control system configured to actuate the at least one motor to drive the drive system and thereby control movement of the staple advancing and forming assembly, the control system having first, second, and third predetermined motor force thresholds for each of the respective first, second, and third stages of operation of the drive system, and the control system being configured to modify a force applied to the drive system by the at least one motor during each of the stages of operation based on the corresponding predetermined motor force threshold.

2. The surgical stapling system of claim 1, wherein the staple advancing and forming assembly comprises
    a staple advancing assembly configured to distally advance the distal-most staple of the plurality of staples and configured to move the distal-most staple from the closed configuration to the open configuration, the staple advancing assembly comprising a pusher and an anvil, and
    a staple former configured to form the distal-most staple around tissue.

3. The surgical stapling system of claim 2, wherein, during the first stage of operation, the drive system drives the pusher distally from a proximal position to an intermediate position and drives the anvil from a proximal position to a distal-most position.

4. The surgical stapling system of claim 2, wherein, during the second stage of operation, the drive system drives the pusher distally from an intermediate position to a distal-most position such that the distal-most staple is moved from the closed configuration to the open configuration.

5. The surgical stapling system of claim 1, wherein each of the first, second, and third predetermined motor force thresholds comprises a maximum motor force threshold for the corresponding stages of operation.

6. The surgical stapling system of claim 5, wherein the control system is configured to stop movement of the drive system when the motor force exceeds the maximum motor force threshold during each of the first, second, and third stages.

7. The surgical stapling system of claim 1, wherein the drive system has a fourth stage of operation in which the drive system proximally retracts the staple advancing and forming assembly to release the distal-most staple.

8. The surgical stapling system of claim 7, wherein the staple advancing and forming assembly includes a staple former configured to form the distal-most staple around tissue, and, during the fourth stage of operation, the drive system proximally retracts the staple former to release the distal-most staple.

9. The surgical stapling system of claim 7, wherein the control system has a predetermined minimum force threshold during the fourth stage of operation, and the control system is configured to stop proximal retraction of the staple advancing and forming assembly when the motor force is less than a minimum motor force threshold.

10. A surgical stapling system, comprising:
    an electromechanical tool shaft assembly having
        an instrument shaft,
        a discharge channel at a distal end thereof,
        a staple stack disposed within the instrument shaft and comprising a plurality of staples in a folded delivery configuration,
        a staple advancing assembly extending through the instrument shaft and configured to feed a distal-most staple of the staple stack into the discharge channel and configured to move the distal-most staple from the folded delivery configuration into an open configuration, and
        a staple forming assembly configured to move the distal-most staple from the open configuration to a tissue-engaging configuration;
    a drive system operably coupled to the electromechanical tool shaft assembly and operably coupled to at least one motor configured to drive the staple advancing assembly and the staple forming assembly, the drive system having a plurality of stages of operation including a first stage of operation in which the drive system drives the staple advancing assembly to advance the distal-most staple of the plurality of staples, a second stage of operation in which the drive system drives the staple advancing assembly to move the distal-most staple from the closed configuration to an open configuration, and a third stage of operation in which the drive system drives the staple forming assembly to move the distal-most staple from the open configuration to the tissue-engaging configuration; and a control system configured to actuate the drive system and thereby control movement of the staple advancing assembly and the staple forming assembly, the control system having at least one predetermined motor force threshold for each of the first, second, and third stages of operation of the drive system, and the control system being configured to modify a force applied to the drive system by the at least one motor during at least one stage of operation when the force applied to the drive system exceeds the at least one predetermined motor force threshold, the force measured by a torque sensor coupled to the at least one motor and in operable communication with the control system.

11. The surgical stapling system of claim 10, wherein the at least one predetermined motor force threshold comprises a maximum motor force threshold for at least one of the first, second, and third stages of operation.

12. The surgical stapling system of claim 11, wherein the control system is configured to stop movement of the drive system when the motor force exceeds the maximum motor force threshold during at least one of the first, second, and third stages.

13. The surgical stapling system of claim 10, wherein drive system is disposed within a housing coupled to a proximal end of the instrument shaft.

14. The surgical stapling system of claim 10, wherein the drive system comprises a first housing on a robotic arm having the at least one motor disposed therein, and a second housing on a proximal end of the instrument shaft and having at least one connector for coupling to the at least one motor in the first housing.

15. A surgical stapling system, comprising:
a staple shaft assembly having a shaft with a plurality of staples disposed therein in a closed configuration, the staple shaft assembly including a staple advancing and forming assembly;
a drive system operably coupled between at least one motor and the staple advancing and forming assembly, the drive system having a plurality of stages of operation including a first stage of operation in which the drive system drives the staple advancing and forming assembly to advance a distal-most staple of the plurality of staples, a second stage of operation in which the drive system drives the staple advancing and forming assembly to move the distal-most staple from the closed configuration to an open configuration, and a third stage of operation in which the drive system drives the staple advancing and forming assembly to form the distal-most staple around tissue; and a control system configured to actuate the at least one motor to drive the drive system and thereby control movement of the staple advancing and forming assembly, the control system having at least one predetermined motor force threshold for at least one of the first, second, and third stages of operation of the drive system, and the control system being configured to continuously monitor a force applied to the drive system during the first, second, and third stages of operation, and to modify a force applied to the drive system by the at least one motor during the at least one stage of operation based on the at least one predetermined motor force threshold.

16. The surgical stapling system of claim 15, wherein the staple advancing and forming assembly comprises
a staple advancing assembly configured to distally advance the distal-most staple of the plurality of staples and configured to move the distal-most staple from the closed configuration to the open configuration, the staple advancing assembly comprising a pusher and an anvil, and
a staple former configured to form the distal-most staple around tissue.

17. The surgical stapling system of claim 16, wherein, during the first stage of operation, the drive system drives the pusher distally from a proximal position to an intermediate position and drives the anvil from a proximal position to a distal-most position.

18. The surgical stapling system of claim 15, wherein the drive system has a fourth stage of operation in which the drive system proximally retracts the staple advancing and forming assembly to release the distal-most staple.

19. The surgical stapling system of claim 18, wherein the staple advancing and forming assembly includes a staple former configured to form the distal-most staple around tissue, and, during the fourth stage of operation, the drive system proximally retracts the staple former to release the distal-most staple.

20. The surgical stapling system of claim 18, wherein the control system has a predetermined minimum force threshold during the fourth stage of operation, and the control system is configured to stop proximal retraction of the staple advancing and forming assembly when the motor force is less than a minimum motor force threshold.

* * * * *